(12) United States Patent
Zhou

(10) Patent No.: US 11,957,726 B2
(45) Date of Patent: Apr. 16, 2024

(54) PHARMACEUTICAL COMPOSITION FOR CONTROLLING BLOOD SUGAR

(71) Applicant: BEIJING HEBABIZ BIOTECHNOLOGY CO., Inc., Beijing (CN)

(72) Inventor: James Zhou, Westport, CT (US)

(73) Assignee: BEIJING HEBABIZ BIOTECHNOLOGY CO., INC., Beijing (CN)

( * ) Notice: Subject to any disclaimer, the term of this patent is extended or adjusted under 35 U.S.C. 154(b) by 92 days.

(21) Appl. No.: 16/645,679

(22) PCT Filed: Sep. 8, 2017

(86) PCT No.: PCT/CN2017/100985
§ 371 (c)(1),
(2) Date: Mar. 9, 2020

(87) PCT Pub. No.: WO2019/047141
PCT Pub. Date: Mar. 14, 2019

(65) Prior Publication Data
US 2020/0276258 A1    Sep. 3, 2020

(51) Int. Cl.
*A61K 36/815* (2006.01)
*A61K 31/155* (2006.01)
*A61K 31/7048* (2006.01)
*A61K 36/889* (2006.01)
*A61K 36/8945* (2006.01)
*A61P 3/10* (2006.01)

(52) U.S. Cl.
CPC .......... *A61K 36/815* (2013.01); *A61K 31/155* (2013.01); *A61K 31/7048* (2013.01); *A61K 36/889* (2013.01); *A61K 36/8945* (2013.01); *A61P 3/10* (2018.01); *A61K 2236/331* (2013.01)

(58) Field of Classification Search
None
See application file for complete search history.

(56) References Cited

U.S. PATENT DOCUMENTS 5,019,580 A * 5/1991 Iwu ...................... C07D 453/06
546/183

FOREIGN PATENT DOCUMENTS

| CN | 1718233 A | 1/2006 |
|---|---|---|
| CN | 1977944 A | 6/2007 |
| CN | 105029410 A | 11/2015 |
| CN | 103583656 B | 1/2016 |
| CN | 106666728 A | 5/2017 |
| CN | 107094834 A | 8/2017 |

OTHER PUBLICATIONS

English translation of Zhang (CN 1977944 A) 2007.*
Iranloye (Journal of Diabetes Mellitus (2013), vol. 3, No. 4, pp. 221-226).*
Luo (Life Sciences (2004), vol. 76, pp. 137-149).*
Rojas (Diabetology & Metabolic Syndrome (2013), vol. 5 No. 6, 15 pages).*
Shen et al., "Application of Traditional Chinese Medicine External Therapy and Food Therapy on Diabetes Treatment", Chinese Journal of Experimental Traditional Medical Formulae, vol. 21, No. 1, Jan. 2015.
Yin et al., "Preparation of Wolfberry—Chinese Yam Compound Beverage", College of Bioengineering, Henan University of Technology, vol. 52, No. 11, Jun. 2013.
International search report for patent application No. PCT/CN2017/100985 dated May 10, 2018.

* cited by examiner

*Primary Examiner* — Susan Hoffman
(74) *Attorney, Agent, or Firm* — Bachman & LaPointe, P.C.

(57) ABSTRACT

A pharmaceutical composition or a health food composition for controlling blood sugar, raw materials of which include *dioscoreae* rhizome, medlar, and coconut oil. A preparation method for the composition includes: mixing *dioscoreae* rhizome and a decoction thereof with medlar for homogenization, pulverization and drying, and mixing the resultant product with coconut oil and water, followed by baking and drying. Further disclosed are a pharmaceutical preparation or a health food including the composition and an excipient, and a use of the composition in the preparation of a pharmaceutical preparation or a health food for reducing or eliminating diabetic conditions.

15 Claims, 1 Drawing Sheet

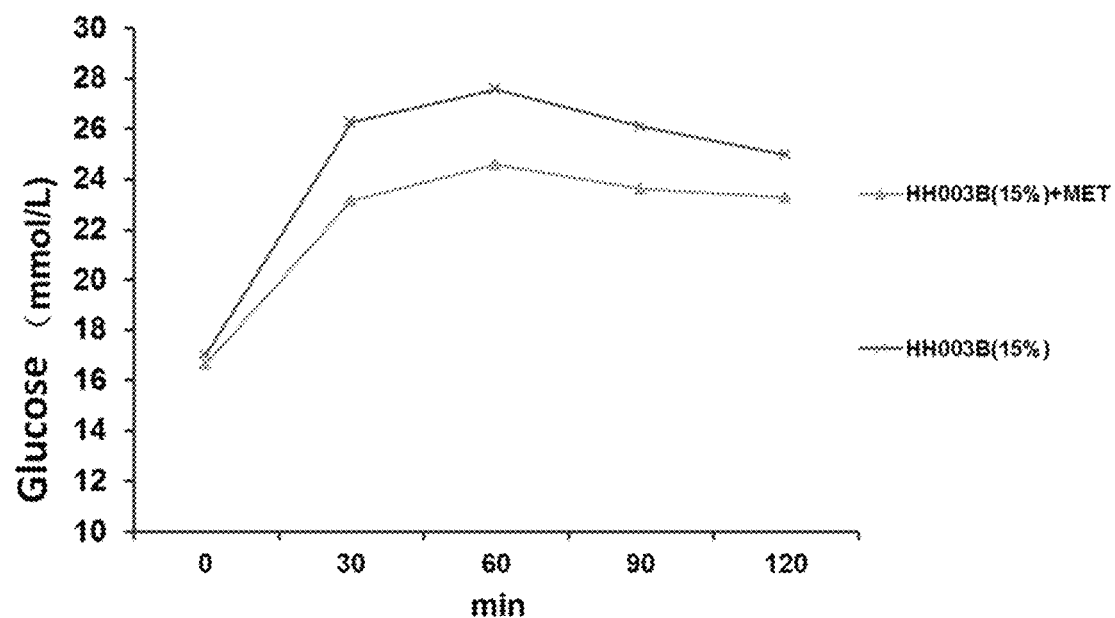

PHARMACEUTICAL COMPOSITION FOR CONTROLLING BLOOD SUGAR

TECHNICAL FIELD

The invention belongs to the field of medicine and health food. In particular, the invention relates to a drug mixture and a health food mixture, including *dioscoreae* rhizoma, lycii fructus and coconut oil, which are used to control blood sugar and, in particular, to eliminate the disease condition of diabetes.

TECHNICAL BACKGROUND

Lycii fructus, also known as *lycium* fruit, produced in tianjin, henan, hebei, shanxi, ningxia and other places, is *lycium* solanaceae deciduous shrub fruit. lycii fructus contains 14 kinds of amino acids, the medicine is sweet, warm, and contains betaine jasmin, acid berry red pigment and other components, has the effect of anti-aging.

*Dioscoreae* rhizoma, also known as yam, potato, mountain yam, huaishan, huaishan medicine, *dioscoreae* rhizoma ranks in the genus of Dioscoreaceae. The medicinal property of *dioscoreae* rhizoma is sweet, even, have nourishing strong, aid digestion, collect empty sweat, the effect that stops diarrhea, lung empty cough, urinate short frequency, spermatorrhea, women with underlying diseases and Chronic enteritis of indigestion.

Lycii fructus and discoreae rhizome are also commonly used in traditional Chinese medicine formulations or dietary formulas for the treatment of diabetes, in fact, according to Shanshan shen etc. (Journal of Chinese experimental formulae, 2015, 21 (1): 209), the most crude drugs used to treat diabetes are *notoginseng* radix et rhizoma, *dioscoreae* rhizoma, lemon, lycii fructus. However, the crude drugs are complex in many formulations, for example, the hypoglycemic formula involved in the Chinese patent CN103583656B includes margarita powder, eriocauli flos, lycii fructus, moslae herba, rehmanniae radix praeparata, white duck, *dioscoreae* rhizoma and other raw drugs. It is difficult to control the quality of many raw materials and products, and it is not easy to have a stable and accurate effect.

Yanli Yin etc. (Hubei Agricultural Science, 2013, 52 (11): 2637) reported the development of compound beverage of lycii fructus and *dioscoreae* rhizoma. However, the efficacy of this beverage in the treatment of diabetes is uncertain. After a long and arduous research and also some luck, the inventor unexpectedly discovered that the combination of *dioscoreae* rhizoma, lycii fructus and coconut oil could not only effectively control blood sugar, but also effectively eliminate many diseases of diabetes. In addition, the preparation technology of the combination is relatively simple, makes it easy to control the quality of the product, and also convenient to shape into various shapes, which is convenient for individuals to carry and take.

SUMMARY OF THE INVENTION

The purpose of the invention is to provide a new mixture which can be used as a drug or a health food to control blood sugar, etc. In addition, the invention also provides a preparation method, a pharmaceutical preparation or a health food and a therapeutic application of the mixture.

In the first aspect, the invention provides a drug mixture or a health food mixture for controlling blood sugar, which includes *dioscoreae* rhizoma, lycii fructus and coconut oil. The mixture mentioned above can be a drug mixture or a health food mixture.

The mixture in the first aspect of the invention is preferably composed of *dioscoreae* rhizoma, lycii fructus and coconut oil.

In the mixture of the first aspect of the invention, the optimal weight ratio of *dioscoreae* rhizoma, lycii fructus and coconut oil is 30~70:5~40:5~40, and the more optimal is 40~60:10~30:10~30.

The mixture in the first aspect of the invention is preferably prepared by the following steps:
(1) Decoct *dioscoreae* rhizoma with water to obtain *dioscoreae* rhizoma and its decocting liquid;
(2) *Dioscoreae* rhizoma and its decoction liquid were mixed with lycii fructus to obtain pulverized product;
(3) After pulverized product is dried, it is mixed with water and coconut oil and optionally shaped, and then baked and dried at high temperature.

The optimal temperature is 100~200° C., the more optimal is 120~160° C., such as 130° C.

In the second aspect, the invention provides a preparation method of the mixture in the first aspect of the invention, which includes the following steps:
(1) Decoct *dioscoreae* rhizoma with water to obtain *dioscoreae* rhizoma and its decocting liquid;
(2) *Dioscoreae* rhizoma and its decoction liquid were mixed with lycii fructus to obtain pulverized product;
(3) After pulverized product is dried, it is mixed with water and coconut oil and optionally shaped, and then baked and dried at high temperature.

In the method of the second aspect of the invention, the optimal temperature is 100~200° C., the more optimal is 120~160° C., such as 130° C.

In the third aspect, the invention provides a product, which is a pharmaceutical preparation, comprising a mixture and acceptable excipients to pharmaceutical in the first aspect of the invention; In addition, the invention also provides a product, which is a health food, comprising a mixture and acceptable addition to food in the first aspect of the invention.

The product in the third aspect of the invention is preferably a tablet, a pill or a biscuit.

In the fourth aspect, the invention provides application in the preparation of products of the mixture in the first aspect of the invention, and the product mentioned above is used to alleviate the diabetes condition. The product can be a pharmaceutical preparation or a health food, preferably, the product is a third party product of the invention.

In the fifth aspect, the invention provides a method to alleviate diabetes condition, which includes giving the mixture mentioned in the first aspect of the invention to individuals in need. Individuals can be humans or other mammals, preferably humans.

The product is preferably used to eliminate diabetes condition in the application of fourth aspect or the method of the fifth aspect of the invention.

The diabetes is optimal a type 2 diabetes in the application of fourth aspect or the method of the fifth aspect of the invention.

In the application of fourth aspect or the method of the fifth aspect of the invention, disease conditions include increased fasting insulin level, increased free fatty acid level and/or increased glycosylated hemoglobin level.

In addition, disease conditions also include some elevated inflammatory cytokines and/or other metabolic indicators.

In the application of fourth aspect or the method of the fifth aspect of the invention, the mixture in the first aspect of the invention is preferably used in combination with the drug for treating diabetes, among which the preferable drug for treating diabetes is metformin or empagliflozin.

In the first aspect, the invention provides a pharmaceutical mixture or a health food mixture, which includes *dioscoreae* rhizoma, lycii fructus and coconut oil.

The mixture mentioned above is used for controlling blood glucose, especially for alleviating or even eliminating the diabetes condition, and can be used as drug or active raw material, or as raw material for health food. The mixture can be a drug mixture or a health food mixture.

In this article, lycii fructus refer to the fruit of *lycium* barbarum shrub of the *lycium* in the solanaceae family unless otherwise indicated. In the present invention, lycii fructus is preferred to be dry lycii fructus. More preferably, the water content of lycii fructus is 5~20% (w/w), still more preferably, the water content of the lycii fructus is 10~15% (w/w). Technicians can dry lycii fructus with high moisture content on the market into raw materials that meet the requirements of the above moisture content through oven baking or freeze-drying.

In this article, *dioscoreae* rhizomas refer to the rhizome of *dioscorea*, unless other indication. The commercially available *dioscoreae* rhizoma can be used in the present invention directly.

In this article, unless otherwise indicated, coconut oil refers to oil extracted from the endosperm of the palm plant coconut. Most of the fatty acid in coconut oil is high boiling, usually at above 230° C., and the smoke point is about 177° C.

The mixture in the first aspect of the invention is preferably composed of *dioscoreae* rhizoma, lycii fructus and coconut oil, water can be introduced into this mixture during the preparation process, but should be removed in the product. So the mixture in the first aspect of the invention does not contain water.

The mixture in the first aspect of the invention is preferably prepared by including the following steps:
(1) Decoct or steam *dioscoreae* rhizoma with water to obtain *dioscoreae* rhizoma and its decocting liquid;
(2) *Dioscoreae* rhizoma and its decoction liquid were mixed with lycii fructus to obtain pulverized products;
(3) After pulverized product is dried, it is mixed with water and coconut oil and optionally shaped, and then baked and dried at high temperature.

The *dioscoreae* rhizoma and its decoction liquid are included in the mixture in the first aspect of the invention. Lycii fructus don't need cook. It's better to repeat the homogenate at low and high speed cause *dioscoreae* rhizoma and lycii fructus are hard to smash.

The crushing product can be mixed with water and coconut oil unshaped, but preferably shaped, such as pieces, blocks or other forms such as cookies or bars, and then baked and dried at high temperature. It can be pressed into shape by mold.

The temperature is between the boiling point of water and coconut oil, preferably between the boiling point of water and the smoking point of coconut oil.

This temperature can remove the introduced moisture and essentially keep the coconut oil. In the first aspect, the optimal temperature is 100~200° C., more optimal is 120~160° C., such as 130° C.

In the second aspect, it provides a preparation method of the mixture in the first aspect of the invention, which includes the following steps:

(1) Decoct or steam *dioscoreae* rhizoma with water to obtain *dioscoreae* rhizoma and its decoction liquid;
(2) *Dioscoreae* rhizoma and its decoction liquid were mixed with lycii fructus to obtain pulverized products;
(3) After pulverized product is dried, it is mixed with water and coconut oil and optionally shaped, and then baked and dried at high temperature.

In the method of the second aspect of the invention, the weight ratio of *dioscoreae* rhizoma, lycii fructus and coconut oil is 30~70:5~40:5~40, and preferably is 40~60:10~30:10~30.

In addition, it also preferably includes the pretreatment steps of *lycium* barbarum and *dioscoreae* rhizoma in the method in the second aspect of the invention.

Among them, the pretreatment steps of *lycium* barbarum include drying step (especially commercially available *lycium* barbarum), such as the moisture content of dried *lycium* barbarum is 5~20% (w/w), optimal is 10~15% (w/w). Among them, the extraction step of *dioscoreae* rhizoma includes washing its surface.

In the third respect, the invention provides a product, which is a pharmaceutical preparation, comprising a mixture in the first aspect of the invention and pharmaceutically acceptable excipients; In addition, the invention also provides a product, which is a health food, comprising a mixture in the first aspect of the invention and acceptable additions to food.

In this article, the term "pharmaceutically acceptable excipients" includes pharmaceutically acceptable carriers, excipients, diluents, etc., which are compatible with the active ingredients of the drug. It is well known to technical personnel in this field to use pharmaceutically acceptable excipients to prepare pharmaceutical preparations. The pharmaceutical preparations mentioned above uses the mixture in the first aspect of the invention as the active ingredient, combine the mixture and pharmaceutical acceptable excipients (such as the well known carrier, excipients, thinner, etc.) together, and made into various preparations, optimization for solid and liquid preparations, such as tablets, pills, capsules (including sustained release or delayed release form), powder, suspension agent, granulation, syrup, emulsion, suspending liquid and other dosage forms and various sustained-release dosage form to oral dosage forms.

In this article, the term "acceptable addition for food" includes acceptable carriers, excipients, diluents, flavoring agents, colorants, flavoring agents, etc., which are compatible with food health care active ingredients. The mixture in the first aspect of the invention can be direct food or food raw material, such as biscuit itself, or can be added to food or food raw material, such as coating the surface of other food or mixing with other food.

In the products of the third aspect of the invention, optimal is capsules, pills or biscuits.

Preferably the third party product of the invention may also include other drugs or health-care active ingredients for the prevention and/or treatment of diabetes.

In the fourth aspect, the invention provides the application of the mixture in the first aspect of the invention in the preparation of the product, which can be used to relief diabetes condition and preferably to eliminate it. The product can be a pharmaceutical preparation or a health food. Accordingly, in the fifth aspect, the invention provides a method for alleviating the diabetes condition and preferably provides a method for eliminating the diabetes condition, which includes giving the mixture of the first aspect of the invention to individuals in need.

In this paper, alleviating the disease condition refers to the reduction in the degree of disease condition of an individual who takes the mixture in the first aspect of the invention compared with the group who does not take the mixture in the first aspect of the invention, which can be experimentally verified by the significant reduction in the degree of disease condition of the group who takes the mixture in the first aspect of the invention compared with the group who does not take the mixture. The degree of alleviation can be large or small, not necessarily to the extent of a normal individual.

In this paper, the elimination of disease condition refers to the fact that the corresponding disease condition index of the sick individual after taking the mixture in the first aspect of the invention reaches the normal range with that of the non-sick individual, which can be verified experimentally-by the fact that there is no significant difference between the sick group taking the mixture in the first aspect of the invention and the corresponding disease condition index of the normal group.

Individuals in need are diabetes individuals who need to be treated; and the product can be taken orally.

The diabetes condition is preferably a type 2 diabetes condition in the application of the fourth aspect and the method of the fifth aspect of the invention.

Disease conditions preferably include increased fasting insulin level, increased free fatty acid level and/or increased glycosylated hemoglobin level in the application of the fourth aspect and the method of the fifth aspect of the invention.

In addition, disease conditions include elevating of some associated inflammatory cytokines (e.g., il-8) and/or other metabolic indicators (e.g., uric acid) indicating disease status.

Preferably, in the application of the fourth aspect or the method of the fifth aspect of the invention, the mixture in the first aspect of the invention can be used alone or in combination with a drug for treating diabetes. For example, the mixture in the first aspect of the invention is used in combination with metformin or empagliflozin.

The beneficial effect of the invention is that the combination of *dioscoreae* rhizoma, lycii fructus and coconut oil can not only effectively control blood sugar, but also eliminate many conditions of diabetes. The preparation process is simple, easy to control the quality of products, easy to shape into various shapes, easy for individuals to carry and take.

The invention quotes the existing public literatures, which are intended to describe the invention more clearly. The full text of the literatures is included in the invention, as if its full text has been repeatedly described in this invention.

For ease of understanding, the present invention is described below through specific embodiments. In particular, these descriptions are illustrative and do not limit the scope of the invention. Other technical schemes of the invention may also be obtained by utilizing the method described in the embodiment of the invention. According to the description in this manual, many changes of the invention are obvious to technicians in the field.

BRIEF DESCRIPTION OF THE DRAWING

FIG. 1 shows the blood glucose levels of HH003B (15%) group and the combined administration group (HH003B (15%)+MET) rats given 2 g/kg of glucose by gavage 12 hours after fasting without water, and then measured at each time.

DETAILED DESCRIPTION

The plant raw materials and chemical reagents in particular embodiments are conventional materials purchased from the market.

Example 1: Preparation of HH003

Weigh the cleaned *dioscoreae* rhizoma 180 g, add 540 ml (3 times the amount) water, heat to boil, keep boiling state for 30 min, put at room temperature, the container is not completely sealed, then get a total of about 350 ml *dioscoreae* rhizoma and decoction, refrigerate it for usage.

Take 60 g lycii fructus and *dioscoreae* rhizome and its decoction liquid mentioned above into VITAMIX0109 refiner (available from VITA-MIX Corp), grind at a low speed (1000 rpm) for 1 min, and then a high speed (20000 rpm) for 3 min, and then repeat a low-speed and high-speed again for 4 times.

HH003 dry powder will get after the crushing product mentioned above dried at 50° C., and then wet the dry powder with water, whose weight is 15% of the HH003 dry powder. Granulation with No. 1 sieve, and then dry 2 hours at 50° C., and consolidation with No. 1 sieve. Finally HH003 particles are prepared.

Example 2: Preparation of HH003B

Referring to the method of implementing case 1, the difference is: the *dioscoreae* rhizoma's weight is 210 g, the added water is 500 ml, and lycii fructus weight is 70 g. Mix 60 g crushing product after dried at 50° C., with 30 ml (30 g) water and coconut oil 20 ml (16 g) well, and cut them into small pieces. Bake these small pieces for 10 minutes to dry at 130° C., and then put them at room temperature to get HH003B.

Example 3: Pharmacodynamic Experiment

Wistar rats were bred adaptively for 1 week. The subjects were randomly divided into the normal Control group (10) and the modeling group (60) according to their body weight from the second week. The normal Control group (Control) was fed with basic feed, and the model group was fed with high-fat and high-sugar feed. After 4 weeks, the model group received intraperitoneal injection of 30 mg/kg streptozotocin (STZ) and continued to eat a high-fat diet, while the control group received intraperitoneal injection of citric acid-sodium citrate buffer at the same volume and continued to eat a normal diet. On the 9th weekend, rats fasted overnight, measured FBG and insulin levels, and calculated the insulin index (ISI). The model would be successfully established if the fasting blood glucose (>) was 11.1 mmol/L and the ISI was decreased.

The successfully modeled rats were randomly divided into Model group, Metformin hydrochloride group, HH003 group, and HH003B group, with 10 rats in each group. The last three groups were given corresponding drugs, metformin hydrochloride group was given a gavage 200 mg/kg daily, HH003 and HH003B group was given drug by feeding, and 30% of the normal feed was replaced by HH003 and HH003B of the high-fat and high-sugar feed separately (about 13 g/d/kg), all the groups were administered for 4 weeks in a row. Fasting but gave water after the last dose, and then weighted the rats after 12 hours. Detected the content of fasting insulin (Insulin), separated the serum, detected the high-density lipoprotein (HDL), free fatty acid (FFA) and glycosylated hemoglobin (GHB).

As shown in table 1, after 4 weeks of administration of various drugs, fasting insulin level in Model rats was significantly increased compared with that in Control rats. HH003B could significantly reduce fasting insulin level in rats and reach a level not significantly different from that of normal rats, while none of the other drugs could do that. Compared with the Control group, FFA level in the serum of Model rats was significantly increased, and HH003B could significantly reduce FFA level of free fatty acids in the serum of rats and reach a level not significantly different from that of normal rats, while other drugs could not do that. The glycosylated hemoglobin GHB level of the Model group was significantly higher than that of the Control group. HH003B could significantly reduce the glycosylated hemoglobin GHB level of the rats and reach the level not significantly different from that of the normal rats. Metformin and HH003 could also significantly reduce the GHB level of the rats but still significantly higher than that of the normal rats. Thus, HH003B can eliminate the disease condition of type 2 diabetes, while metformin and HH003 can only improve the disease condition of type 2 diabetes to a certain extent. In addition, metformin can significantly increase HDL level, and HH003B can also increase HDL level but not significantly, suggesting that both of them have an improvement effect on lipid metabolism.

TABLE 1 influence of drugs on biochemical indexes of rat model

| | Insulin (uIU/ml) | HDL (mmol/L) | FFA (mmol/L) | GHB (mmol/L) |
|---|---|---|---|---|
| Control | 25.42 ± 4.65 | 0.57 ± 0.2 | 0.42 ± 0.05 | 11.50 ± 0.96 |
| Model | 33.28 ± 6.00** | 0.57 ± 0.2 | 0.54 ± 0.06*** | 16.11 ± 0.6*** |
| Metformin | 31.15 ± 6.28 | 0.74 ± 0.15*# | 0.56 ± 0.03*** | 15.07 ± 0.85***# |
| HH003 | 29.64 ± 5.49 | 0.58 ± 0.25 | 0.5 ± 0.09* | 13.38 ± 0.9***### |
| HH003B | 25.90 ± 6.73# | 0.72 ± 0.22 | 0.44 ± 0.06## | 11.94 ± 2.15### |

Compared with the normal control group, *$P < 0.001$, $P < 0.01$, *$P < 0.05$;
Compared with the model group, #$P < 0.05$, ##$P < 0.01$, and ###$P < 0.001$.

Example 4: Combined Drug Use Experiment

HH003B alone in large amounts (30%, basically replacing one meal) has a significant effect on improving the disease condition of type 2 diabetes. Reducing the amount of HH003B also has an improvement, but it is not as good as the large amount of it. So a trial of combination with existing diabetes drugs was conducted. Empagliflozin group was given by gavage 1 mg/kg once a day. HH003B group (15%) was given drug by feeding, and 15% of the normal feed was replaced by HH003B of the high-fat and high-sugar feed separately (about 7 g/d/kg). Combined drug group (HH003B (15%)+Emp) was given Empagliflozin by gavage 1 mg/kg, plus high fat and sugar feed, whose 15% ordinary feed was instead of HH003B (about 7 g/kg/d), other are the same as the implementation example 3 experiments. HbA1c was determined at the end of the experiment.

As shown in table 2, Empagliflozin alone had no effect on glycosylated hemoglobin in patients with diabetes, but in combination with HH003B with reduced dose showed a significant effect on the control of glycosylated hemoglobin elevation.

TABLE 2 influence of drugs on glycosylated hemoglobin (HbA1c) in rat model

| Group | HbA1c (mg/dl) |
|---|---|
| Control | 6.03 ± 0.18 |
| Model | 7.32 ± 0.12### |
| Empagliflozin | 7.01 ± 0.17 |
| HH003B (15%) | 6.86 ± 0.25* |
| HH003B (15%) + Emp | 6.21 ± 0.15* |

Compared with the model group, *$P < 0.001$, $P < 0.01$, *$P < 0.05$;
Compared with the normal control group, #$P < 0.05$, ##$P < 0.01$, and ###$P < 0.001$.

Example 5: Preliminary Study on Mechanism

15% of the normal feed was replaced by HH003B of the high-fat and high-sugar feed (about 7 g/d/kg) in the HH003B (15%) group, while in the combined group (HH003B (15%)+MET), metformin hydrochloride was given by gavage 200 mg/kg daily, plus 15% of the normal feed was replaced by HH003B of the high-fat and high-sugar feed (about 7 g/d/kg), and the rest were the same as the experiment in case 3.

At the end of the experiment, glucose tolerance and serum triglyceride (TG), low-density lipoprotein (LDL), uric acid (UA) and IL-8 were measured.

As shown in table 3 and FIG. 1, HH003B combined with metformin can further reduce blood glucose, triglyceride (TG), low-density lipoprotein (LDL) IL-8, uric acid (UA) and other levels, which may also have an effect on the diabetic condition or its potential complications, indicating that HH003B and metformin have different mechanisms of action.

TABLE 3 influence of HH003B combined with metformin on serum biochemical indexes of rats

| Group | TG (mmol/L) | LDL (mmol/L) | IL-8 (pg/mL) | UA ($\mu$mol · L$^{-1}$) |
|---|---|---|---|---|
| HH003B (15%) | 1.60 ± 0.40 | 0.28 ± 0.02 | 46.38 ± 2.93 | 293.752 |
| HH003B (15%) + MET | 0.98 ± 0.32 | 0.20 ± 0.02 | 40.51 ± 2.13 | 129.343 |

The invention claimed is:
1. A drug mixture or health food mixture for controlling blood glucose, comprising *dioscoreae* rhizoma, lycii fructus and coconut oil, wherein the mixture is in the form of a tablet, pill or biscuit, and wherein the mixture contains a weight ratio of the *dioscoreae* rhizoma, the lycii fructus and the coconut oil of 30~70:5~40:5~40.

2. A method for preparing the mixture of claim 1, comprising the following steps:
   (1) decoct or steam *dioscoreae* rhizoma with water to obtain *dioscoreae* rhizoma and its decocting liquid;
   (2) mixing *dioscoreae* rhizoma and its decoction liquid with lycii fructus to obtain pulverized product;
   (3) drying the pulverized product, and then mixing with water and coconut oil, and then baking and drying at a high temperature of 100~200° C.

3. A method for preparing the mixture of claim 1, comprising the following steps:
   (1) decoct or steam *dioscoreae* rhizoma with water to obtain *dioscoreae* rhizoma and its decocting liquid;
   (2) mixing the *dioscoreae* rhizoma and its decoction liquid with lycii fructus to obtain pulverized product;
   (3) drying the pulverized product is dried, and then mixing with water and coconut oil, and then baking and drying at a high temperature of 60~200° C.

4. A pharmaceutical preparation or health food containing the mixture of claim 1 and medically acceptable auxiliary or food materials.

5. A method for preparing a pharmaceutical preparation or health food for alleviating diabetic disease, comprising applying the mixture of claim 1 to the preparation of pharmaceutical preparations or health food.

6. A method for alleviating the condition of diabetes, comprising administering the mixtures of claim 1 to a person in need.

7. The method of claim 6, wherein the person in need has type 2 diabetes.

8. The method of claim 6, wherein the condition includes increased fasting insulin level, increased free fatty acid level, increased glycosylated hemoglobin level, and/or conditions indicated by relevant inflammatory factors or other metabolic indicators.

9. The method of claim 6, wherein the administering step comprises administering the person in need with a combination of the mixture of claim 1 and a drug for the treatment of diabetes selected from metformin or Empagliflozin.

10. The mixture of claim 1, wherein the mixture consists of *dioscoreae* rhizoma, lycii fructus and coconut oil.

11. The mixture of claim 1, wherein the weight ratio is 40~60:10~30:10~30.

12. The method of claim 2, wherein the high temperature is 120~160° C.

13. The mixture of claim 1, wherein the weight ratio is 210:70:16.

14. The mixture of claim 1, further comprising at least one of metformin, empagliflozin, and combinations thereof.

15. The mixture of claim 1, wherein the *dioscoreae* rhizome and the lycii fructus are present as a blended powder.

* * * * *